United States Patent [19]

Gay

[11] Patent Number: 5,258,409

[45] Date of Patent: Nov. 2, 1993

[54] TREATMENT FOR SANITIZING AQUEOUS SOLUTIONS

[75] Inventor: Walter A. Gay, Cheshire, Conn.

[73] Assignee: Olin Corporation, Cheshire, Conn.

[21] Appl. No.: 840,411

[22] Filed: Feb. 24, 1992

[51] Int. Cl.$^5$ ............... C07C 211/63; C07C 211/64; A01N 33/12; A61K 31/14
[52] U.S. Cl. .................... 514/642; 504/158; 514/643; 564/281; 564/282; 564/288; 564/291
[58] Field of Search ............ 71/67; 514/642; 564/291; 504/158

[56] References Cited

U.S. PATENT DOCUMENTS

| | | | |
|---|---|---|---|
| 2,688,583 | 9/1954 | Darragh et al. | 71/67 |
| 3,356,526 | 12/1967 | Waldman et al. | 564/291 |
| 3,819,656 | 6/1974 | Barie, Jr. et al. | 564/291 |
| 4,098,602 | 7/1978 | Seymour et al. | 71/67 |
| 4,444,790 | 4/1984 | Green et al. | 514/642 |
| 4,569,800 | 2/1986 | Stanley et al. | 564/291 |

OTHER PUBLICATIONS

Huech et al., "Bacteriostatic, Fungistatic, and Algistatic Activity of Fatty Nitrogen Compounds" *Applied Microbiology*, vol. 14, No. 3 (1966) pp. 308-319.
Royal A. Cutler, Eberhard B. Cimijotti, Thomas J. Okolowich and William F. Wetterau, entitled "Alkylbenzyldimethylammonium Chlorides-a Comparative Study of the Odd and Even Chain Homologues", Chem. Spec. Mfg. Assoc. Proc. Ann. No. 53; (1966) at pp. 102-113.
R. L. Shriner, R. C. Fuson and D. Y. Curtin, entitled "The Systematic Identification of Organic Compounds", 4th Edition (1948) at pp. 228-229.
W. J. Pope and S. J. Peachy, entitled "Asymmetric Optically Active Nitrogen Dextro-and Lavo-a-Benzylphenylallylmethylammonium Iodides and Bromides" appearing in Journal Chem. Soc. 1127 (1899) at pp. 1127-1131.
Disinfectants (Water) for Swimming Pools, JAOAC 52 836 (1969) p. 4.045.

*Primary Examiner*—Glennon H. Hollrah
*Assistant Examiner*—P. O'Sullivan
*Attorney, Agent, or Firm*—William A. Simons

[57] ABSTRACT

A sanitizing composition for aqueous solutions comprising an dialiphatic dimethylammonium salt having an effective bactericidal activity at a concentration below about 50 ppm by weight in the medium to be sanitized during a maximum contact time not exceeding 60 seconds.

6 Claims, No Drawings

TREATMENT FOR SANITIZING AQUEOUS SOLUTIONS

FIELD OF THE INVENTION

This invention relates to the rapid sanitization of aqueous solutions by treatment with effective dosages of select dimethyl quaternary ammonium salts.

BACKGROUND OF THE INVENTION

The water in swimming pools is constantly recirculated and fresh water is normally added only to maintain the desired volume. Although the water is usually filtered continuously to keep it free from suspended matter, it frequently contains bacteria and treatment to control the bacteria count is necessary to prevent infection.

The main disinfectant used in swimming pools at present is chlorine, which is effective, but suffers from the disadvantages that it may cause eye irritation and also has to be added at frequent intervals to maintain an effective concentration for killing bacteria.

Ozone has also been used as a disinfectant, but again frequent or continuous dosing is necessary, and contact with high concentrations at the point where ozone is injected into the pool is unpleasant and can cause headaches.

One of the first quaternary ammonium compounds synthesized was ethyltrimethylammonium iodide [W. J. Pope and S. J. Peachy, Journal Chemical Society, 1127 (1899)]. Since then, a wide variety of commercially significant quaternary ammonium salts have been prepared by reacting a tertiary amine with an alkyl halide or alkyl-hydrogen sulfate. The most important quaternary ammonium salts (commonly referred to as "QUATS") are the alkyl-trimethyl QUATS, dialkyl-dimethyl QUATS, trialkyl-methyl QUATS, and tetraalkyl QUATS. The most common markets for these QUATS are as surfactants, as fabric softeners, as thixotropic clays and for hair treatment. Still another use for QUATS is in the biocide market as disinfectants (household, institutional, industrial, hospital), as cooling tower microbiocides, as preservatives, antiseptics and laundry bacteria-stats where they are used at high concentrations and long contact times with the bacteria.

Quaternary ammonium compounds generally have four carbon atoms covalently linked to a nitrogen atom. The resulting cationic species is generally associated with an anionic segment (X) such as a chloride, bromide or methosulfate, and the like.

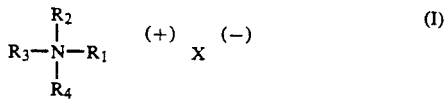

In the above formula (I) $R_1$, $R_2$, $R_3$ and $R_4$ are aliphatic groups that may be alike or different, substituted or unsubstituted, saturated or unsaturated, cyclic or acyclic.

Heretofore, the use of QUATS in swimming pools has been limited to the control of algae, e.g. SUN® Algae Preventer (an alkyl-dimethyl-benzylammonium chloride) and HTH® Non-Foaming Algaecide Concentrate [poly[oxyethylene(dimethyliminio)ethylene(dimethyliminio)ethylene dichloride]]. Table I shows the reported use of a variety of QUATS to control a variety of algae. While algae control in swimming pools is highly desirable, it is well recognized that these algae are non-pathogenic and do not affect human health. This is not true for bacteria, since their presence in swimming pool water is known to cause infections affecting the skin, eyes, throat, nose, ears and intestines of humans in contact with the contaminated water. To prevent such bacterial infections, these harmful bacteria must be killed rapidly if they are present in a swimming pool. Indeed, the standard test method for disinfectants in swimming pools (A.O.A.C. test method 4.047–4.055) requires that a swimming pool bactericide kills high levels of bacteria in only 30 seconds of contact. In practice, this rapid bactericidal activity must be accomplished at low concentrations, e.g. 50 ppm or less, to avoid the potential of producing objectional, aesthetically unpleasing turbid swimming pool water having a high total organic carbon (TOC) content.

TABLE I (Prior Art)
INHIBITING CONCENTRATIONS (IN PPM) OF
FATTY NITROGEN COMPOUNDS FOR SOME ALGAE*

| Compound | CH. Vulgaris | Stigeoclonium Species | A. Cylindrica | OS. Tenuis |
|---|---|---|---|---|
| Benzethonium Chloride | 3 | 1 | 1 | 1 |
| Benzalkonium Chloride | 1 | 0.7 | 1 | 0.6 |
| Dodecyltrimethylammonium Chloride | 50 | 5 | 5 | 0.5 |
| Dodecylbenzyldimethylammonium Chloride | 0.2 | 0.2 | 0.2 | 0.2 |
| Cocobenzyldimethylammonium Chloride | 2 | 0.5 | 2 | 0.7 |
| Didecyldimethylammonium Chloride | 2 | 0.7 | 0.2 | 0.7 |

*H. H. Hueck, D.M.M. Adema and J. R. Wiegmann, Appl. Microbiol., 14(3), 308(1966)

As summarized in Table II below, published scientific literature on representative classes of quaternary ammonium compounds as antimicrobial agents conclude that high concentrations of QUATS are needed just to inhibit the growth of *E. coli* bacteria; i.e. to function as bacteria-stats, not bacteria-cides. Lower concentrations of antimicrobial QUATS become effective as bactericides only when the contact-time is excessive [R. A. Cutler, E. B. Cimijotti, T. J. Okolowich and W. F. Wetteran, C.S.M.A. Proceedings of the 53rd Annual Meeting, 102 (1966)].

TABLE II (Prior Art)
INHIBITING CONCENTRATIONS (in ppm) OF FATTY
NITROGEN COMPOUNDS FOR *E. COLI* BACTERIA*

| Compound | Concentration |
|---|---|
| Benzethonium chloride | 1,000 |
| Benzalkonium chloride | 200 |
| Dodecyltrimethylammonium chloride | 500 |

TABLE II-continued (Prior Art)
INHIBITING CONCENTRATIONS (in ppm) OF FATTY NITROGEN COMPOUNDS FOR *E. COLI* BACTERIA*

| Compound | Concentration |
| --- | --- |
| Dodecylbenzyldimethylammonium chloride | 750 |
| Cocobenzyldimethylammonium chloride | 225 |
| Didecyldimethylammonium chloride | 225 |

*H. J. Hueck, D.M.M. Adema and J. R. Wiegmann, Appl. Microbiol., 14(3), 308(1966)

SUMMARY OF THE INVENTION

It is an object of the present invention to provide a process for sanitizing aqueous solutions.

Another object of the invention is to rapidly sanitize aqueous solutions, such as in swimming pools, hot tubs and spas, to safe levels during a maximum contact time of 60 seconds.

These and other objects of the invention are accomplished in a process for sanitizing aqueous solutions whereby the bacteria count is rapidly lowered by treating said solutions with a select dimethyl quaternary ammonium salt having an effective bactericidal activity during a maximum contact time of 60 seconds.

DETAILED DESCRIPTION OF THE INVENTION

In accordance with the invention there is rapid sanitization of aqueous solutions with a dimethyl quaternary ammonium salt in which the cation is represented by formula II as follows:

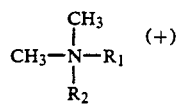

$$\begin{array}{c} CH_3 \\ | \\ CH_3-N-R_1 \\ | \\ R_2 \end{array} \quad (+) \qquad (II)$$

wherein $R_1$ is a mixed aliphatic hydrocarbon radical preferably derived from a fatty acid or its hydrogenated analogue; and $R_2$ is selected from the group consisting of an aliphatic hydrocarbon radical having from 2 to 20 carbon atoms or a mixed aliphatic hydrocarbon radical preferably derived from a fatty acid or its hydrogenated analogue. The anion in these salts can be any biocidally acceptable anion such as a halide, sulfate, methosulfate, acetate, borate, glucamate and so forth. The preferred halides are chlorides and bromides. By practice of the invention, one is able to rapidly and economically sanitize water in swimming pools, hot tubs and spas to safe and acceptable bacteria levels.

Mixed aliphatic hydrocarbons radicals as used herein, include, but are not limited to, alkyl groups that may be alike or different, substituted or unsubstituted, saturated or unsaturated, cyclic or acyclic, linear or branched. Mixed aliphatic hydrocarbon radicals derived from a fatty acid or its hydrogenated analogue include products obtained from animal, vegetable and marine sources such as, but not limited to, tallow, soybean oil, coconut oil, palm oil, palm kernel oil, fish oil, rapeseed oil and tall oil. Also included are fatty acid aliphatic hydrocarbons derived from petroleum sources. Hydrogenated analogues include products in which at least some, if not all, the unsaturated groups have been reduced to saturated groups. Chemical compositions of the fatty acid contained in typical fats and oils is set forth in TABLE III.

TABLE III

Composition of Fatty Acids Obtained from Fats and Oils
(Percent by Weight)

| Fatty Acid Composition | Tallow | Soybean Oil | Coconut Oil | Palm Kernel Oil | Tall Oil |
| --- | --- | --- | --- | --- | --- |
| Saturated | | | | | |
| $C_8$ Caprylic | — | — | 6 | 3 | — |
| $C_{10}$ Capric | — | — | 7 | 4 | — |
| $C_{12}$ Lauric | — | — | 46 | 49 | — |
| $C_{14}$ Myristic | 3 | — | 18 | 18 | — |
| $C_{16}$ Palmitic | 27 | 10 | 11 | 8 | — |
| $C_{18}$ Stearic | 18 | 4 | 3 | 2 | 3 |
| Total: | 48% | 14% | 91% | 84% | 3% |
| Unsaturated | | | | | |
| $C_{18:1}$*Oleic | 42 | 25 | 7 | 14 | 59 |
| $C_{18:2}$*Linolenic | 4 | 54 | 2 | 2 | 38 |
| $C_{18:3}$*Linolenic | 1 | 7 | — | — | — |
| Total | 47% | 86% | 9% | 16% | 97% |

*Number of carbon atoms:Number of double bonds (Chemical Economics Handbook - SRI International, 1988)

The quaternary ammonium salts (QUATS) used according to the invention are those dimethyl QUATS described above which have an effective bactericidal activity at relatively low levels of concentration to achieve at least a 99.99% kill of *E. coli* bacteria (i.e. leaving less than 100 colony forming units (CFUs) remaining per milliliter) during a brief contact time. Thus, the term "effective bactericidal activity" as used in the specification and claims herein, means such activity, at the specified QUAT concentration and contact time, as will result in at least a 99.99% destruction of *E. coli* bacteria. Surprisingly, unlike similar prior art QUATS, it has been found that certain selected dimethyl QUATS exhibit such effective bactericidal activity at concentrations below 50 ppm (parts by weight of QUAT per one million parts of aqueous solution treated) and during a contact time not exceeding 60 seconds. Thus, any such QUAT which meets these criteria of bactericidal activity can be used in the sanitizing compositions of the invention. The test used herein as a standard to verify and demonstrate the bactericidal activity of the QUATS of the invention is a variation of the American Organization of Analytical Chemists (AOAC) procedure 4.047 entitled "Disinfectants (Water) for Swimming Pools". The variation, which makes the test more stringent, consists in adding 200 ppm of calcium carbonate hardness and 100 ppm alkalinity to the water in order to simulate typical hardness and alkalinity in swimming pool water.

As indicated earlier with reference to formula II, $R_2$ can be an aliphatic hydrocarbon radical having from 2 to 20 carbon atoms. In accordance with the preferred embodiments of the invention, this aliphatic radical contains from 3 to 18, and still more preferably, 4 to 17 carbon atoms.

The QUATS of the invention are those which have effective bactericidal activity when used in levels of concentration below 50 ppm, and preferably from about 5 to about 25 ppm. In accordance with one specific embodiment the most bactericidally active QUATS of the invention are effective at concentrations as low as about 10-20 ppm. It will become apparent, however, that depending on the particular aqueous medium being treated and various external factors, redosing of the QUAT used may be necessary from time to time in order to maintain the desired concentration. For example, a heavily used swimming pool may require redosing at more frequent intervals than another pool of the same size which is used only occasionally or lightly.

The effective bactericidal activity of the QUATS of the invention is realized upon a brief contact time with the aqueous medium being treated. Specifically, the maximum contact time needed is 60 seconds; and in accordance with the preferred embodiments of the invention, a contact time of 30 seconds is sufficient, at the appropriate concentration level, as detailed hereinbefore, to realize the 99.99% kill of E. coli bacteria.

Since long term control of bacteria growth in the water of swimming pools is readily achieved according to the present invention, the necessity for providing expensive equipment for constantly metering controlled amounts of chlorine in the water is avoided. It is only necessary to dissolve the QUAT of the invention in the water and to ensure a uniform concentration in the range defined. Furthermore, at the very low concentrations found to be effective, the QUATS of the invention have no effect on the eyes, no objectionable odor or taste, and do not bleach clothing as may happen with the use of chlorine or ozone.

In testing and screening various QUATS for bactericidal activity, various procedures and screening methods have been used, and these are briefly described below.

Screening Protocol—The screen protocol used for the invention and for the evaluation of comparative QUATS is summarized immediately below. In all cases, the various compounds are contacted with $10^6$ E. coli bacteria per ml of water at specific concentrations for a preset time. The primary screen uses 100 ppm of the compound at a 5 minute contact time; the secondary screen, 20 ppm at a 1 minute contact time; the tertiary screen, 5-50 ppm at a 30 second contact time.

Inoculum Preparation—E. coli ATCC 11229, is grown on TSA slants 18-24 hours at 35° C. Slants are washed with 10 mL sterile saline (0.85%) and centrifuged at 10,000 rpm for 10 minutes. The supernatant is discarded; the culture is resuspended in 10 mL saline and centrifuged two more times. Final resuspension is in sterile RO water. The culture suspension is adjusted to an optical density (OD) of 0.2 at 550 nm, approximately $2 \times 10^8$ cells/mL, using a Bausch & Lomb Spectronic 20.

Primary Screen—Solutions of test compounds at 100 ppm active ingredient are prepared in Barnstead purified water. Using an Eppendorf 10-100 µL pipetter, 100 µL portions are pipetted into sterile glass test tubes, 15×150 mm. Ten microliters of a 1:10 dilution of the 10 CFU/mL E. coli suspension are added to give a final concentration of $10^5$ CFU/100 µL or $10^6$ CFU/mL. Solutions are mixed gently and held at ambient temperature. A positive control is prepared in the same manner using saline as the diluent. After 5 minutes, 9.9 mL Nutrient Broth (Difco) is added to dilute test compounds to 1 ppm and solutions are plated on Nutrient Agar using a Spiral Plater (Spiral System Instruments, Inc., Bethesda, Md.). Subcultures of 10 µL are also made to 10 mL Nutrient Broth. Both broth dilutons are incubated at 35° C. and visually examined for growth after 48 hours. Plates are incubated 18 hours at 28° C. to facilitate reading with a laser counter. The lower detection limit is 25 CFU/mL times the dilution plated. In this screen, test solutions are diluted 1:100; therefore, the detection limit is 2,500 CFU/mL. Compounds demonstrating $10^3$-fold or better reduction in bacteria in 5 minutes are then tested in the secondary screen.

Secondary Screen—Test solutions, 20 ppm active ingredient, are prepared in AOAC buffer (see AOAC test method for "Disinfectants[Water] for Swimming Pools"). The buffer is adjusted to pH 7.5 and 200 ppm calcium hardness and 100 ppm alkalinity are added. The diluent is prepared in autoclaved Barnstead Nanopure II water. Ten milliliter portions are pipetted into test tubes and 40 µL of the inoculum adjusted to OD 0.2 is added. Tubes are vortexed 4 times during the exposure time. After 1 minute, 1 mL is transferred to 9 mL AOAC neutralizer (azolectin and polysorbate 80) and vortexed vigorously. Controls are run to insure that compounds are effectively neutralized. Neutralized solutions are plated in duplicate, 1 mL/plate, in Tryptone Glucose Extract Agar (TGEA). The plates are incubated at 35° C. for 48 hours and manually counted with the aid of a Quebec Colony Counter. Based on plating 1 mL of the $10^1$ dilution in duplicate, the detection limit is 5 CFU/mL. Compounds demonstrating $10^3$-fold or better reduction in bacteria in 1 minute are tested in the tertiary screen.

Tertiary Screen—The tertiary screen differs only from the secondary screen in the length of time organisms are exposed to test compounds and the concentrations tested. Compounds are tested for activity in 30 seconds at concentrations of 5 to 50 ppm or less.

TESTING OF PRIOR ART QUATS

A wide variety of tetraalkyl, trialkyl-methyl and alkyl-trimethyl QUATS were tested for bactericidal activity using primary and/or secondary screening. The number of carbons in the alkyl groups ranged from a low of 2 to as high as 18 carbons. All the prior art QUATS tested were available and purchased commercially. The results of the tests are shown in Tables III, IV and V. As the data in these tables clearly demonstrate, none of the tested QUATS exhibited sufficient bactericidal activity to qualify, by itself, as an effective swimming pool sanitizer at the required low level of concentration.

TABLE IV (Prior Art)
BACTERICIDAL TESTING OF TETRAALKYL QUATS*

| Compound | Log-Reduction of E. coli |
|---|---|
| Tetramethylammonium chloride | 0 |
| Tetraethylammonium bromide | 0 |
| Tetrabutylammonium bromide | 0 |
| Tetrahexylammonium chloride | 0 |
| Tetraoctylammonium bromide | insoluble (a) |
| Tetraoctadcylammonium bromide | insoluble (a) |

*Primary screen - $10^6$ E. coli/ml at start.
(a) Tested at 10 and 100 ppm.

TABLE V (Prior Art)
BACTERICIDAL TESTING OF TRIALKYL-METHYL QUATS*

| Compound | Test Procedure | Log-Reduction of E. coli |
|---|---|---|
| Tributylmethylammonium chloride | Primary | 0 |
| Trioctylmethylammonium chloride | Primary | >3 |
|  | Secondary | 0 |
| Tridecylmethylammonium chloride | Primary | >3 |
|  | Secondary | 0 |
| Tridodecylmethylammonium chloride | Primary | >3 |
|  | Secondary | <2 |
| Benzyl-bis(hydrogenated | Secondary | <2 |

TABLE V-continued (Prior Art)
BACTERICIDAL TESTING OF TRIALKYL-METHYL QUATS*

| Compound | Test Procedure | Log-Reduction of E. coli |
|---|---|---|
| tallow) methylammonium chloride | | |

*$10_6$ E. coli/ml at start.

TABLE VI (Prior Art)
BACTERICIDAL TESTING OF ALKYL-TRIMETHYL QUATS*

| Compound | Test Procedure | Log-Reduction of E. coli |
|---|---|---|
| Octyltrimethylammonium chloride | Secondary | <2 |
| Decyltrimethylammonium chloride | Secondary | <2 |
| Dodecyltrimethylammonium chloride | Secondary | <2 |
| Tetradecyltrimethylammonium chloride | Secondary | <2 |
| Hexadecyltrimethylammonium chloride | Primary | <2 |
|  | Secondary | <2 |
| Octadecyltrimethylammonium chloride | Secondary | <2 |
| Cocotrimethylammonium chloride | Secondary | <2 |
| Tallowtrimethylammonium chloride | Secondary | <2 |
| Soyatrimethylammonium chloride | Secondary | <2 |
| Benzyltrimethylammonium chloride | Secondary | <2 |

TESTING OF PRIOR ART DIMETHYLDIALKYL QUATS

A number of dimethyl QUATS were also tested for bactericidal activity, which have been reported in the prior art to exhibit the highest biocidal activity of the dialkyldimethyl QUATS. Specifically, the dimethyl QUATS tested were those in which the two alkyl groups are octyl and/or decyl. The tested dimethyl QUATS were synthesized in the laboratory using well-known prior art methods. The results of these tests, summarized in Table VI below, again clearly indicated that the bactericidal activity of these particular dimethyl QUATS is insufficient for them to be considered as swimming pool sanitizers.

TABLE VII (Prior Art)
BACTERICIDAL TESTING OF REPORTED BIOLOGICAL ACTIVE DIALKYLDIMETHYL QUATS*

| Compound | CFU/ml Remaining |
|---|---|
| Dioctyldimethylammonium chloride | >$10^4$ |
| Decyloctyldimethylammonium chloride | >$10^4$ |
| Didecyldimethylammonium chloride | >$10^3$ |

*$10^6$ E. coli/ml at start; 20 ppm concentration, 30 seconds contact-time; tertiary screen

QUALIFYING TEST FOR MIXED ALIPHATIC HYDROCARBON DIMETHYL QUATS

The mixed aliphatic hydrocarbon dimethyl QUATS have shown effective bactericidal activity that is unexpected based upon the bactericidal activity shown for the dialkyldimethyl QUATS of the prior art discussed previously. The following examples are illustrative of the sanitizing compositions of the various QUATS of the invention.

DICOCODIMETHYL QUATS

A number of select dialkyldimethyl QUATS were tested for bactericidal activity at 20 ppm against $10^6$ E. coli/ml for one minute contact time in the secondary screen. The $R_1$ and $R_2$ radicals in the tested salts were the same i.e. ditallow, di(hydrogenated tallow) (a tallow in which the unsaturated groups have been reduced), and a disoyaalkyl of fatty acid origin. All of these tested select dialkyldimethyl ammonium chloride salts left greater than $10^4$ E. coli/ml.

A coco radical group derived from coconut fatty acids was then used as the alkyl group in the dialkyldimethyl QUAT. This coco group is a mixture of $C_8$ to $C_{18}$ hydrocarbons with a preponderance of $C_{12}$ and $C_{14}$ hydrocarbon groups in proportions approximately of the sources from which they are derived. A typical alkyl group composition of coco segment of dicocodimethyl ammonium chloride is octyl 6%; decyl 7%; dodecyl 46%; tetradecyl 18%; hexadecyl 11%; octadecyl 3%; and unsaturated $C_{18}$ 9%.

When dicocodimethyl ammonium chloride was tested under the same conditions as the dialkyldimethyl QUATS above (i.e. 20 ppm against $10^6$ E. coli/ml in the secondary screen and 1 minute contact time) less than 40 CFU/ml bacteria were observed remaining. Commerically available dicocodimethyl QUATS (e.g. ARQUAD®2C-75, EXXON®Q-2C, M-QUAT®2475, and ADOGEN®462) were tested at 20 ppm concentration against $10^6$ E. coli/ml for one minute contact time. The results of these tests showed less than 50 CFU/ml remained, thus demonstrating an unexpected high bactericidal activity of the dicocodimethyl QUATS.

Additional testing of the dicocodimethyl QUAT using a 30 second contact time at concentrations varying from 10 to 50 ppm was performed and the results are shown TABLE VIII which follows. These test results show that the high bactericidal activity is maintained even at the short contact time. Thus, the dicocodimethyl ammonium QUAT when used in accordance with the invention would qualify when used alone as a highly effective swimming pool sanitizer.

TABLE VIII

BACTERICIDAL TESTING OF DICOCODIMETHYLAMMONIUM CHLORIDE AT 30 SECOND CONTACT TIME*

| CONCENTRATION (ppm) | CFU/ml REMAINING |
|---|---|
| 50 | <10 |
| 20 | 30 |
| 10 | 90 |

*$10^6$ E. coli/ml at start.

HYDROGENATED TALLOW DIMETHYL QUATS

Tallow is a mixture of $C_{14}$ to $C_{18}$ hydrocarbon groups with a preponderance of saturated $C_{16}$ and $C_{18}$ and unsaturated $C_{18}$. Hydrogenated tallow is tallow in which the number of unsaturated groups has been at least partially reduced.

Di(hydrogenated tallow)-dimethyl QUATS were tested for bactericidal activity at 20 ppm against $10^6$ E. coli/ml for 1 minute contact time in the secondary screen. The radicals $R_1$ and $R_2$ (see formula II) in the tested compounds were both hydrogenated tallow hydrocarbons. Under the test conditions using the secondary screen, greater than $10^4$ E. coli/ml survived this showing that they have unacceptable bactericidal activity similar to the dialkyldimethyl QUATS shown in Table VII.

When one of the (hydrogenated tallow) radicals was replaced with a single aliphatic hydrocarbon radical in the di(hydrogenated tallow)-dimethyl QUAT salt, surprisingly strong bactericidal activity was noted. Thus, when (hydrogenated tallow)-2-ethylhexyl-dimethyl ammonium methosulfate was tested under the same conditions as the di(hydrogenated tallow)-dimethyl QUATS, it was observed that only 15 *E. coli*/ml survived. Thus, replacement of one of the (hydrogenated tallow) groups by a 2-ethylhexyl group gives a product that would qualify, when used alone, as an effective pool sanitizer.

TABLE IX summarizes the data obtained from testing (hydrogenated tallow)-2-ethylhexyl-dimethyl ammonium methosulfate at various concentrations (5–50 ppm) against $10^6$ *E. coli*/ml for 30 seconds using a teriary screen. As seen, the exceptionally high bactericidal activity is maintained even at shorter contact-time. For comparison, the corresponding chloride salt was also tested and it was found that, like its methosulfate analog, it too is highly active as a bactericide at low concentrations and short contact-time (Note Table X). This demonstrates that the bactericidal activity is not dependent on the particular anion in the QUATS used according to the invention.

TABLE IX
BACTERICIDAL TESTING OF
(HYDROGENATED TALLOW)-
2-ETHYLHEXYL-DIMETHYLAMMONIUM
METHOSULFATE
AT 30 SECONDS CONTACT TIME*

| Concentration (ppm) | CFU/ml REMAINING |
|---|---|
| 50 | 10 |
| 20 | 5 |
| 10 | 55 |
| 5 | 1000 |

*Tertiary screen - $10^6$ *E. coli*/ml at start.

TABLE X
BACTERICIDAL TESTING OF
(HYDROGENATED TALLOW)-
2-ETHYLHEXYL-DIMETHYLAMMONIUM CHLORIDE
AT 30 SECONDS CONTACT TIME*

| Concentration (ppm) | CFU/ml Remaining |
|---|---|
| 50 | 10 |
| 20 | 5 |
| 10 | 5 |
| 5 | 50 |

*Tertiary screen - $10^6$ *E. coli*/ml at start.

When a (hydrogenated tallow) group is replaced with a linear aliphatic hydrocarbon, such as an octyl group, to yield the product (hydrogenated tallow)ocyldimethylammonium chloride, it is expected that similar high bactericidal activity would be obtained.

The following example is provided to illustrate the bactericidal activity of the dimethyl QUATS of the invention when used as sanitizers in an actual operating swimming pool.

(Hydrogenated tallow)-2-ethylhexyl-dimethylammonium methosulfate was tested for bactericidal efficacy in a 1,500 gallon pool maintained at 200 ppm hardness, 100 ppm alkalinity, and pH 7.2–8.0. A sand filter was operated at 12 hours on and 12 hours off. Before QUAT addition, the pool water had $1.7 \times 10^6$ CFU/ml count of mixed bacteria at the start of the experiment; 4 hours after the QUAT was added, the mixed bacteria count was less than 10 CFU/ml. After 1 month of operation, the QUAT concentration was analyzed at 18 ppm vs. the original 20 ppm charge concentration. After 3 weeks of operation, a sample of water was removed and contacted with $10^6$ *E. coli*/ml for 30 seconds. Only 10 CFU/ml remained, thus demonstrating the long term efficacy of the product.

By virtue of the rapid bactericidal activity of some of the select dimethyl QUATS of the invention, they are especially efficacious for use as sanitizers in swimming pools, hot tubs, spas, and the like, used for human contact. The QUATS of the invention would also qualify as fast acting disinfectants in hospital applications, such as for sanitizing hard surfaces, in those cases where a rapid lowering of the bacteria count may be required.

Many quaternary ammonium salts used according to the invention are available commercially. Others can be prepared by well known substitution reactions involving alkyl halides and tertiary amines. Further details concerning preparation of these QUATS can be found for example in "The Systematic Identification of Organic Compounds" by R. L. Shriner, R. C. Fuson, and D. Y. Curtin, 4th Edition, 1948, pages 228 and 229, which is incorporated herein by reference.

Sanitizing compositions or formulations incorporating the dimethyl QUATS disclosed herein as the active ingredient can be prepared using prior art diluents, colorants, fragrances, foam suppressants, and such other functional or non-functional additions as desired or necessary for the particular utility.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

I claim:

1. A process for sanitizing water in swimming pools, hot tubs, and spas whereby the bacteria count in said water is rapidly lowered comprising:
   treating said water with a quaternary ammonium salt selected from the group consisting of (hydrogenated tallow) 2-ethylhexyl dimethyl ammonium chloride, (hydrogenated tallow) 2-ethylhexyl dimethyl ammonium methosulfate, and dicoco dimethyl ammonium chloride, the concentration of said quaternary ammonium chloride, the concentration of said quaternary ammonium salt being less than 50 ppm by weight of said water and sufficient to result in effective bactericidial activity in said water for contact time of not in excess of 60 seconds.

2. The process of claim 1 wherein said contact time is not in excess of 30 seconds.

3. The process of claim 1 wherein said concentration of quaternary ammonium salt is from about 5 to about 25 ppm by weight of said water.

4. The process of claim 1 wherein said quaternary ammonium salt is (hydrogenated tallow) 2-ethylhexyl dimethyl ammonium chloride.

5. The process of claim 1 wherein said quaternary ammonium salt is (hydrogenated tallow) 2-ethylhexyl dimethyl ammonium methosulfate.

6. The process of claim 1 wherein said quaternary ammonium salt is dicoco dimethylammonium chloride.

* * * * *